United States Patent
Singh

(10) Patent No.: US 9,616,026 B2
(45) Date of Patent: Apr. 11, 2017

(54) SUSTAINED RELEASE FORMULATIONS OF SOTALOL

(75) Inventor: Bramah N. Singh, Encino, CA (US)

(73) Assignee: The Roshni Singh 2015 Trust, San Francisco, CA (US)

( * ) Notice: Subject to any disclaimer, the term of this patent is extended or adjusted under 35 U.S.C. 154(b) by 3 days.

(21) Appl. No.: 12/231,896

(22) Filed: Sep. 5, 2008

(65) Prior Publication Data

US 2009/0047346 A1 Feb. 19, 2009

Related U.S. Application Data

(63) Continuation of application No. 11/134,089, filed on May 20, 2005, now abandoned.

(60) Provisional application No. 60/573,367, filed on May 20, 2004.

(51) Int. Cl.
| A61K 9/20 | (2006.01) |
| A61K 9/00 | (2006.01) |
| A61K 47/36 | (2006.01) |

(52) U.S. Cl.
CPC ............ *A61K 9/205* (2013.01); *A61K 9/0053* (2013.01); *A61K 47/36* (2013.01)

(58) Field of Classification Search
CPC ....... A61K 47/36; A61K 9/0053; A61K 9/205
See application file for complete search history.

(56) References Cited

U.S. PATENT DOCUMENTS

| 4,792,452 | A | 12/1988 | Howard et al. | |
| 4,871,549 | A | 10/1989 | Ueda et al. | |
| 4,957,745 | A | 9/1990 | Jonsson et al. | |
| 4,994,276 | A | 2/1991 | Baichwal et al. | |
| 5,081,154 | A | 1/1992 | Appelgren et al. | |
| 5,089,526 | A | 2/1992 | Simon et al. | |
| 5,128,143 | A | 7/1992 | Baichwal et al. | |
| 5,135,757 | A | 8/1992 | Baichwal et al. | |
| 5,169,638 | A | 12/1992 | Dennis et al. | |
| 5,399,358 | A * | 3/1995 | Baichwal et al. | ............ 424/464 |
| 6,281,246 | B2 | 8/2001 | Sankaranarayanan | |
| 6,500,457 | B1 * | 12/2002 | Midha ................... | A61K 9/2081 424/451 |
| 2003/0185887 | A1 * | 10/2003 | Chen et al. ................... | 424/471 |
| 2006/0105044 | A1 | 5/2006 | Singh | |

FOREIGN PATENT DOCUMENTS

WO WO 9513055 5/1995

OTHER PUBLICATIONS

Anderson et al., "Sotalol: An important new antiarrhythmic," American Heart Journal, Mar. 1999, pp. 388-409.*
Labhasetwar et al. ("Sotalol Controlled-Release Systems for Arrhythmias: In Vitro Characterization, in Vivo Drug Disposition, and Electrophysiologic Effects" Journal of Pharmaceutical Sciences, vol. 83, No. 2, Feb. 1994, pp. 156-164).*
Anderson J L: Sotalol in life-threatening ventricular arrhythmias: A unique class III antiarrhythmic. Amer. J Cardiol 72:1A-80A, 1993.
Antonaccio M J. Gomoll A W Pharmacology, pharmacodynamics and pharmacokinetics of sotalol. Am J Cardiol 1990; 65:12A-20A.
Atwood, J. Edwin, et al. "Exercise capacity in atrial fibrillation: a substudy of the Sotalol-Amiodarone Atrial Fibrillation Efficacy Trial (SAFE-T)." American heart journal 153.4 (2007): 566-572.
Benditt D G, Williams J H, Jin J et al. For the dl-Sotalol Atrial Fibrillation/Flutter Study Group. Maintenance of sinus rhythm with oral dl-sotalol therapy in patients with symptomatic atrial fibrillation and flutter: A dose-response study. Am J Cardiol 1999; 84:270-176.
Juul-Möller, S., Nils Edvardsson, and Nina Rehnqvist-Ahlberg. "Sotalol versus quinidine for the maintenance of sinus rhythm after direct current conversion of atrial fibrillation." Circulation 82.6 (1990): 1932-1939.
Kato R, Yabek L, Ikeda N, Kannan R, Singh B N. Electrophysiologic effects of dextro- and levo-isomers of sotalol in isolated cardiac muscle and their in vivo pharmacokinetics. J Am Coll Cardiol 1986; 7:116-126.
Kehoe, Richard F., et al. "Safety and efficacy of sotalol in patients with drug-refractory sustained ventricular tachyarrhythmias." The American journal of cardiology 65.2 (1990): 58-64.
Mason, Jay W. "A comparison of seven antiarrhythmic drugs in patients with ventricular tachyarrhythmias." New England Journal of Medicine 329.7 (1993): 452-458.
Movsowitz C, Marchlinski F E. Interactions between implantable cardioverter-defibrillators and class III antiarrhythmic drugs. Am J Cardiol 82:411, 1998; and [0086].
Nademanee K, Feld G, Hendrickson J A, Singh P N, Singh B N: Electrophysiologic and antiarrhythmic effects of sotalol in patients with life-threatening ventricular tachyarrhythmias. Circulation 1985; 72:555-564.
Pacifico A, et al. "Prevention of Implantable Cardioverter-defibrillators and class III agents" N Eng J Med 1999; 340: 1855-1862.
Reimold, Sharon C., et al. "Propafenone versus sotalol for suppression of recurrent symptomatic atrial fibrillation." The American journal of cardiology 71.7 (1993): 558-563.
Sen, Luyi, et al. "Electrophysiological effects of MS-551, a new class III agent: comparison with dl-sotalol in dogs." Journal of Pharmacology and Experimental Therapeutics 285.2 (1998): 687-694.

(Continued)

*Primary Examiner* — Aradhana Sasan
(74) *Attorney, Agent, or Firm* — Knobbe, Martens, Olsen & Bear, LLP

(57) ABSTRACT

Sustained release compositions of sotalol, or a pharmaceutically acceptable salt thereof, are provided. In certain examples, sotalol, or a pharmaceutically acceptable salt thereof, may be administered in an effective amount to provide a therapeutic effect to a patient, such as, for example, a patient suffering from a cardiac disorder. In some examples, sotalol combined with a sustained release system may be administered to provide a sustained release of sotalol for a desired period, e.g., at least about 24 hours.

6 Claims, No Drawings

(56) References Cited

OTHER PUBLICATIONS

Sharma, Param P., Jonnalagedda SM Sarma, and Bramah N. Singh. "Effects of sotalol on the circadian rhythmicity of heart rate and QT intervals with a noninvasive index of reverse-use dependency." Journal of cardiovascular pharmacology and therapeutics 4.1 (1999): 15-21.

Singh B N (Ed). A Symposium: Approaches to Controlling Cardiac Arrhythmias: Focus on Amiodarone, the last 15 Years. Am J Cardiol 1999; 84 (Supp 9A); 1R-174R.

Singh B N, Sarna J S M. Mechanisms of action of antiarrhythmic drugs relative to the origin and perpetuation of cardiac arrhythmias. J Cardiovasc Pharmacol Therpeut 2001; 6(1):69-87.

Singh B N, Vaughan Williams E M. A third class of anti-arrhythmic action. Effects on atrial and ventricular intracellular potentials, and other pharmacological actions on cardiac muscle, of MJ 1999 (sotalol) and AH 3474. Br J Pharmacol 1970; 39:675-687.

Singh B N, Vaughan Williams. The effect of amiodarone, a new anti-anginal drug, cardiac muscle. Brit J Pharmacol 1970; 39; 657-667.

Singh B N. Current antiarrhythmic drugs: An overview of mechanisms of action and clinical utility. J Cardiovasc Electrophysiol 1999; 10:283-301.

Singh B N. Sotalol: Current status and expanding indications. J Cardiovasc Pharmacol Therapeut 1999; 4 (1):59-65.

Singh B N: A Symposium: Controlling cardiac arrhythmias with sotalol, a broad-spectrum antiarrhythmic with beta-blocking effects and class III activity. Am J Cardio 65:1A-11A, 1990.

Singh, Steven N., et al. "Comparison of sotalol versus amiodarone in maintaining stability of sinus rhythm in patients with atrial fibrillation (Sotalol-Amiodarone Fibrillation Efficacy Trial [Safe-T])." The American journal of cardiology 92.4 (2003): 468-472.

Singh B N: Antiarrhythmic action of dl-sotalol in ventricular and supraventricular arrhythmias. J Cardiovasc Pharmacol 2:590, 1992.

Singh B N: Antiarrhythmic actions of amiodarone: A profile of a paradoxical agent. Amer J Cardiol 1996; 78: 41-53.

Singh, B. N., et al. "Sotalol. A review of its pharmacodynamic and pharmacokinetic properties, and therapeutic use." Drugs 34.3 (1987): 311-330.

Singh, Bramah N. "Antiarrhythmic actions of DL-sotalol in ventricular and supraventricular arrhythmias." Journal of cardiovascular pharmacology 20 (1992): S75-hyhen.

Singh, Bramah N. "Atrial fibrillation: epidemiologic considerations and rationale for conversion and maintenance of sinus rhythm." Journal of cardiovascular pharmacology and therapeutics 8.1 suppl (2003): S13-S26.

Singh, Bramah N. "Current antiarrhythmic drugs." Journal of cardiovascular electrophysiology 10.2 (1999): 283-301.

Singh, Bramah N. "Sotalol: A Unique Beta-Blocker with Class III Antiarrhythmic Properties." Beta-Blockers and Cardiac Arrhythmias 5 (1992): 253-292.

Singh, Bramah N., et al. "Amiodarone versus sotalol for atrial fibrillation." New England Journal of Medicine 352.18 (2005): 1861-1872.

Singh, Bramah N., et al. "Multicenter trial of sotalol compared with procainamide in the suppression of inducible ventricular tachycardia: a double-blind, randomized parallel evaluation." American heart journal 129.1 (1995): 87-97.

Singh, Steven N., et al. "Quality of life and exercise performance in patients in sinus rhythm versus persistent atrial fibrillation: a Veterans Affairs Cooperative Studies Program Substudy." Journal of the American College of Cardiology 48.4 (2006): 721-730.

The Cardiac Arrhythmia Suppression Trial (CAST) Investigators: Preliminary report: Effect of encainide and flecainide on mortality in a randomized trial of arrhythmia suppression after myocardial infarction. New Eng J Med 321:406, 1989.

\* cited by examiner

SUSTAINED RELEASE FORMULATIONS OF SOTALOL

CROSS-REFERENCE TO RELATED APPLICATIONS

This application is a continuation of U.S. patent application Ser. No. 11/134,089, filed May 20, 2005, which claims the benefit under 35 U.S.C. §119(e) to U.S. Provisional Application No. 60/573,367, filed May 20, 2004, the entire disclosures of each of which are hereby incorporated by reference herein.

BACKGROUND

For many decades, the clinical significance of prolonged duration of action for drugs used in the control of heart disease has been appreciated. It is recognized that many life-threatening heart disorders occur in recurrent episodes. This pattern is typified by the attacks of angina pectoris (chest pain) and especially disorders of heart rhythm such as ventricular arrhythmias and in particular atrial fibrillation. Indeed, arrhythmia currently is the most common serious disorder of the heart beat. It is responsible for much morbidity as well as mortality. Thus, drug therapies targeting these conditions require continuous drug action without periodic or intermittent lapses due to suboptimal drug concentrations between dosing intervals. There remains a need for better drug formulations to control heart disorders.

SUMMARY

In accordance with a first aspect, a sustained release composition of sotalol, or a pharmaceutically acceptable salt thereof, is disclosed. In certain examples, an oral solid sustained release composition, which may release sotalol over a time period longer than for conventional formulations (e.g., 24 hours or more) is provided. In some examples, the compositions may be ingested orally and may thereby be exposed to one "environment of use," namely the gastrointestinal tract. In other examples, the compositions may be exposed to other "environments of use" (e.g. an aqueous solution of the kind used in in vitro dissolution testing). In certain examples, the sustained release composition comprises sotalol, or a pharmaceutically acceptable salt thereof, and a sustained release system. In some examples, the sotalol, or a pharmaceutically acceptable salt thereof is present in an effective amount to provide a therapeutic effect in a patient. In certain examples, the sustained release system may provide sustained release of sotalol for at least about 24 hours. In some examples, the 24 hour period may be any period that is still a sustained period relative to conventional drug activity duration and/or half-life of sotalol. In certain examples, the sustained release system may be an oral, rectal, topical or parenteral system. In some examples, the sotalol, or a pharmaceutically acceptable salt thereof, may be an analog of sotalol, a derivative of sotalol, a mixture of sotalol constituents, an isomer of sotalol, a racemic mixture of sotalol, or combinations thereof.

In accordance with another aspect, a sustained release composition of sotalol, or a pharmaceutically acceptable salt thereof, is disclosed. In certain examples, a sustained release composition of sotalol, or a pharmaceutically acceptable salt thereof, comprises an effective amount of sotalol, or a pharmaceutically acceptable salt thereof, to provide a therapeutic effect to a patient. In certain examples, the sustained release composition may also include a sustained release excipient system of a heteropolysaccharide gum or a homopolysaccharide gum (or both) that is capable of cross-linking or being cross-linked. In other examples, the sustained release composition may also include an inert pharmaceutical diluent. In yet other examples, the sustained release composition may also include a pharmaceutically acceptable cationic cross-linking agent. In certain examples, the cross-linking agent may be capable of cross-linking with a gum and/or may increase the gel-strength of the gum when exposed to an environmental fluid or environment of use. In certain examples, the sustained release composition may be effective to provide sustained release of sotalol for at least about 24 hours when exposed to the environmental fluid or the environment of use. In some examples, the 24 hour period may be any period that is still a sustained period relative to conventional drug activity duration and/or half-life of sotalol. In certain examples, the sustained release system may be an oral, rectal, topical or parenteral system. In some examples, the sotalol, or a pharmaceutically acceptable salt thereof, may be an analog of sotalol, a derivative of sotalol, a mixture of sotalol constituents, an isomer of sotalol, a racemic mixture of sotalol, or combinations thereof.

In accordance with an additional aspect, a method of preparing a sustained release composition of sotalol is provided. In certain examples, the method includes preparing a sustained release composition of sotalol. The sustained release composition of sotalol may be any of the illustrative forms described herein, e.g., an effective amount of sotalol and a sustained release system. In certain examples, the method may further include combining the sustained release composition, or a pharmaceutically acceptable salt thereof, with a gum to provide a drug/gum ratio determined to provide a desired degree of sustained release. In some examples, the method may also include tableting the combined sotalol and gum such that each tablet includes a dose of sotalol effective to provide a therapeutic effect, e.g., in a human patient, for at least about 24 hours.

In accordance with an additional aspect, a method of preparing a sustained release composition of sotalol is provided. In some examples, the method includes preparing a sustained release system. In certain examples, the method may also include combining the sustained release system with a sotalol, or a pharmaceutically acceptable salt thereof. The sotalol may be any of the illustrative forms described herein, e.g., an effective amount of sotalol, analog or derivative thereof. In certain examples, the method may further include quantifying the combined sustained release system and the sotalol into discrete unit forms such that each unit, regardless of composition, form, route of administration, etc., includes a dose of sotalol effective to provide a therapeutic effect for at least about 24 hours, e.g., effective to provide a therapeutic effect in a human patient in need of treatment for at least about 24 hours.

In accordance with another aspect, a method of treating a patient with a sustained release formulation of sotalol is disclosed. In certain examples, the method includes administering an effective amount of a sustained release dosage form of sotalol, or a pharmaceutically acceptable salt thereof, to the patient. In some examples, the method may further include preparing a sustained release system. In other examples, the method may further include combining the sustained release system with sotalol, or a pharmaceutically acceptable salt thereof. In yet other examples, the method may further include tableting or producing units of the combined sustained release system and sotalol such that each tablet or unit includes a dose of sotalol effective to provide a therapeutic effect, e.g., to a patient in need of treatment, for at least about 24 hours.

It will be recognized by the person of ordinary skill in the art, given the benefit of this disclosure, that the illustrative sustained release compositions described herein represent a significant advance in treatment of certain medical disorders, such as cardiac disorders. Numerous formulations effective to provide sustained release of sotalol for a selected period will be readily selected by the person of ordinary skill in the art, given the benefit of this disclosure.

DETAILED DESCRIPTION

Certain features, aspects and examples of the instant technology are described below with reference to certain illustrative examples. It will be recognized by the person of ordinary skill in the art, given the benefit of this disclosure, that other features, aspects and examples may be included in the illustrative examples described herein.

Throughout this disclosure, the term "sotalol" is often used. This term is intended to refer to various forms, derivatives, isomers, analogs and the like of sotalol, including but not limited to sotalol hydrochloride, a sotalol derivative, a sotalol analog, a sotalol isomer, a racemic mixture of sotalol form, and the like. In particular, any therapeutically effective form of sotalol may be used in any of the sustained release compositions disclosed herein in order to achieve a solid or other dosage form with therapeutic properties that include the benefits of the sustained release formulation described here as well as the unique benefits, if any, of such derivative, analog, isomer or like form. Thus, in an exemplary preferred embodiment, one skilled in the art may employ one of the sustained release formulations and methods described herein but replace sotalol hydrochloride with any permissible combination of D- and L-isomers of sotalol. Such a sustained release formulation may not only have the benefits of a 24 hour release but may also enjoy the unique benefits of reducing unnecessary beta-blockade. The utilization of the sustained release formulation in this manner would allow unprecedented sustained release anti-arrhythmic therapy in patients with structural heart disease and other such conditions where sustained release therapy would be optimal provided that beta-blockade could be reduced. Accordingly, uses of the term "sotalol" throughout this document should be understood to include such analogs, derivatives, isomers, racemic mixtures and the like as context permits. Embodiments of the present compositions produced with such analogs, derivatives, isomers, racemic mixtures, and the like are within the scope of this instant technology.

As used herein, the term "treatment" is intended to encompass, among other things, prophylaxis/prevention, therapy, maintenance, symptom alleviation, and cure. A patient receiving a sustained release sotalol composition and/or treatment may be any living animal organism in need, including primates, in particular humans, and other mammals such as, for example, equines, cattle, swine, sheep, felines, canines, poultry and domestic pets in general.

As used herein, the term "sustained release" indicates that the therapeutically active medicament (sotalol) may be released from the composition at a controlled rate in such a manner that blood levels (that are still below the toxic levels of the medicament) may be maintained at therapeutically beneficial levels over an extended duration of time (e.g., 24 hours or more, thereby providing a single dose, daily dosage formulation.)

As used herein, the term "environmental fluid" in the context of at least certain examples refers to an environmental fluid in which the technology disclosed herein may be properly utilized (e.g., gastrointestinal fluid or fluid used in in vitro dissolution.) The term "environment of use" has the same meaning unless otherwise clear from the context.

As used herein, the term "effective amount" refers to an amount that may provide a desired level of treatment or therapy to a patient in need of treatment for a disease or disorder. For example, an effective amount of the composition may produce some desired therapeutic effect (e.g., reduction of arrhythmia) in at least a sub-population of cells in an animal at a reasonable benefit/risk ratio applicable to any medical treatment. It will be recognized by the person of ordinary skill in the art, given the benefit of this disclosure, that an effective amount for a selected patient may not necessarily be an effective amount for another patient, and that the effective amount selected for a particular patient may depend, at least in part, on the patient's weight, sex, age, health status, drug tolerance and the like. As used herein, the phrase "therapeutically-effective amount" to that quantity of the active medicament (e.g., sotalol hydrochloride or a derivative, isomer, analog or the like form of sotalol). Any illustrative dosages mentioned elsewhere in this disclosure, including the common sotalol dosages mentioned herein, are provided as examples and should not be construed to limit the scope of the technology described herein.

As used herein, the phrase "pharmaceutically acceptable" refers to those compounds, materials, compositions, and/or dosage forms which are, in view of reasonable and current medical and pharmacological standards, suitable for use in contact with the tissues of mammals, such as human beings, and animals without excessive toxicity, irritation, allergic response, or other problem or complication, whereby the benefits associated with use of such compound, materials, compositions and/or dosage forms outweigh the associated risks in a manner that falls within a reasonable benefit/risk ratio. The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting a subject compound from one organ, or portion of the body, to another organ, or portion of the body. Each carrier must be "acceptable" in the sense of being compatible with the other ingredients of the formulation and not injurious to the patient. Many such non-toxic compatible substances may be employed in compositions disclosed herein and specifically in the case of sustained release formulations. Additional carriers and/or additives, etc. (e.g., those necessary beyond the carriers, additives, and excipients, etc., necessary for the sustained release formulation itself) will be dictated by the particular method and composition used to achieve a particular sustained release formulation. The necessity and propriety of additional carriers, additives, excipients, etc., will be readily determined by one skilled and knowledgeable in the art, given the benefit of this disclosure, and optionally considering, for example, the principal elements of the sustained release composition, the reason for adding the additional ingredient, and the effect it may have on the sustained release composition's intrinsic therapeutic and functional properties.

In accordance with certain examples, there have been several approaches to ensure longer dosing intervals. A first approach is the synthesis of compounds that inherently have elimination half-lives exceeding 24 hours. An example of this is the drug amiodarone (1) which has an elimination half-life exceeding 24 hours when given intravenously and over 30 days when administered by mouth. A second approach focuses on markedly increasing the duration of action through a controlled release mechanism without altering the elimination half-life whereby the same cumulative daily dose of a short acting drug (that is administered multiple times during the day) is administered once daily to continuously maintain the tissue and blood levels without significant fluctuations. Such controlled release action is likely to ensure continuous protection against recurrences of disorders such as myocardial ischemia, aberrations of heart rhythm, and abnormal increases in blood pressure in patients with hypertension.

This second approach, which does not involve altering the normal elimination half-life of drugs, has utilized a wide diversity of methods. Various hydrogels, for example have been used in the development of controlled release medicines, some being synthetic, others semi-synthetic, and others of natural origin, all with variable effectiveness in controlling and sustaining drug release after oral ingestion and thereby prolonging the overall increase in the duration of drug action.

In the past, in view of the significant episodic nature of heart disorders, a major objective was to ensure better patient compliance in administering drugs acting on the heart and blood vessels. In recent years, however, there has been an increasing focus on prolonging the time course of the pharmacodynamic properties of such drugs with the continuity of effect over successive dosing intervals. Indeed, this is a critical therapeutic objective in many cardiovascular disorders including cardiac arrhythmias that are life-threatening or that are associated with major morbidities. In this context, the two most commonly used drugs in the control of such arrhythmias are sotalol (2) and amiodarone (1).

Although sotalol has been the prototype of the so-called class III anti-arrhythmic compounds and its unique electrophysiological properties were described in 1970 (2), it is only relatively recently that it has drawn widespread attention as an agent for controlling cardiac arrhythmias (3-7). The reasons are several-fold. For one, the CAST trial (8) and various meta-analytic studies of different electrophysiological classes of compounds have indicated the potentially lethal propensity of sodium-channel blockers when they are used for arrhythmia control in patients with structural heart disease (6). Moreover, extensive experience with the drug amiodarone, widely perceived as also acting principally via lengthening cardiac depolarization and by adrenergic inhibition, has contributed to the increasing shift from the use of class I to class III agents (9, 10).

Sotalol (3-7, 11-13) and amiodarone (1, 9, 10) have now emerged as the two most significant drugs for the control of atrial fibrillation for restoration and maintenance of sinus rhythm (14). They are also the most significant medicaments for the reduction of defibrillator shocks in patients in whom implantable devices are placed for the prevention of sudden cardiac death. However, there are major differences in the overall properties of the two compounds. On the one hand, sotalol has the unique combination of a nonselective beta-blocking property while at the same time effecting prolongation of cardiac repolarization in the atria as well in the ventricles. Sotalol is 100% bioavailable and has an elimination (exclusively renal) half-life of 8-12 hours (administered twice daily). In contrast, amiodarone is structurally and pharmacologically complex, its bioavailability is 30-50%, it is metabolized in the liver and none is excreted by the kidney. It blocks the adrenergic receptors nonspecifically rather than at the direct receptor level. When given orally, the drug prolongs repolarization in most cardiac tissues. Unlike sotalol, amiodarone has a complex pattern of often serious adverse reactions and its elimination half-life is exceedingly long. On the other hand, the prolonged half-life of amiodarone which permits once-daily drug administration, often only 5 days per week, has been associated with the continuous maintenance of sinus rhythm for prolonged periods of time in patients with atrial fibrillation restored to sinus rhythm (10). It is noteworthy that sotalol is as effective as amiodarone in inducing spontaneous conversion of atrial fibrillation to sinus rhythm, and is equally effective as amiodarone in facilitating direct current cardioversion of atrial fibrillation compared to placebo, thus indicating that the drug exerts similar anti-fibrillatory effects in the atrial myocardium with respect to the rhythm disorders known as atrial flutter or fibrillation. However, sotalol in conventional doses has been found to be significantly less effective than amiodarone in maintaining the stability of sinus rhythm in patients with atrial fibrillation restored to sinus rhythm. It is therefore likely that the very much shorter duration of action of sotalol, as compared to amiodarone, is a cause of the lower effectiveness of the drug, since multiple daily doses in this setting typically result in breakthroughs of the arrhythmia under treatment. This shortcoming in the overall property of sotalol is likely to be overcome by the development of a controlled and sustained-release formulation for the release of the compound such as, for example, the illustrative sustained release compositions disclosed herein.

There have been a number of patents and publications that relate to sustained and controlled-release formulations for the release of metoprolol, a beta-blocker, which, unlike sotalol, does not exhibit any effects on cardiac repolarization. Barring the presence of the methylsulphonyl substituent in the para position of the aromatic ring of the sotalol molecule, sotalol and metoprolol are very similar in chemical structure. Various controlled and sustained release formulations for the release of metoprolol have been described, including in a number of patents: U.S. Pat. No. 5,169,638, U.S. Pat. No. 4,792,452, U.S. Pat. No. 4,957,745, U.S. Pat. No. 4,871,549, U.S. Pat. No. 5,081,154, U.S. Pat. No. 4,994,276, U.S. Pat. No. 5,128,143, U.S. Pat. No. 5,135,757 and WO Patent No. 9513055 (entitled "Sustained Release Formulations For 24 Hour Release of Metoprolol", hereinafter and for the purpose of this disclosure only sometimes referred to as the "24 Hour Release Metoprolol Patent"), each of which is hereby incorporated by reference in its entirety for all purposes.

U.S. Pat. No. 5,169,638, and the previously filed U.S. Pat. No. 4,792,452, describe a pH-independent controlled release pharmaceutical formulation in the form of a powder filled capsule, where such powder is basic in character (e.g. metoprolol). The formulation's principle components are a water-soluble salt of polyuronic acid and a pH-independent hydrocolloid gelling agent (such as hydroxypropylmethylcellulose, hydroxypropylcellulose, or methylcellulose). The formulation, free of calcium ions and carbon dioxide producing material, will float in gastric juices, and thus prolong the release of the active powder ingredients.

U.S. Pat. No. 4,957,745 describes a controlled release system for metoprolol that comprises principally a number of beads of metoprolol such that a polymer membrane permeable to metoprolol (e.g. ethylcellulose or a mixture of ethylcellulose and hydroxypropylmethylcellulose) coats each of the beads. The coating, in prescribed amounts, will enable release of metoprolol over a period of at least 15 hours nearly independent of the pH in the pH interval 1-8.

U.S. Pat. No. 4,871,549 describes another controlled release system for metoprolol, a so called "Time Controlled Explosion System" whereby a swelling agent (e.g., a low substituted hydroxypropylcellulose, sodium starch glycolate or carboxymethylcellulose sodium) and a core of the drug metoprolol are coated with a water-insoluble coating material (e.g., ethylcellulose). This facilitates controlled release because the water-insoluble coating ruptures after a definite period of time, commonly referred to as "lag time." The lag time will depend on the relative amount of water-insoluble coating material present. By mixing lag time systems in a particular sustained release preparation, different sustained and controlled release patterns can be achieved.

U.S. Pat. No. 5,081,154 proposes an oral composition of metoprolol succinate that is coated with an anionic polymer comprising about 10% to about 85% by weight and soluble at a pH above 5.5, and about 15% to about 90% by weight of a water-insoluble polymer from the group of quaternary ammonium substituted acrylic polymers. The composition achieves controlled release of the drug in the gastrointestinal tract below the upper part of the small intestine. The 24 Hour Release Metoprolol Patent, focuses on a sustained release excipient system comprising the active medicament (e.g., metoprolol), both heteropolysaccharide and homopolysaccharide gums (e.g., xanthan gum and locust bean gum, respectively), a cross-linking agent (e.g., monovalent or multivalent metal cations, in particular calcium sulfate and sodium chloride), and an inert diluent (e.g., lactose, dextrose, sucrose, or mixtures thereof or other pharmaceutically acceptable saccharides) such that the use of the cross-linking agent with the heteropolysaccharides and homopolysaccharides results in increased gel-strength and thereby provides a sustained release of metoprolol in the environment of use that is suitable for a single dosage, daily administration. The 24 Hour Metoprolol Patent which describes this method incorporates by reference related methods that are now commercially available under the tradename TIMERX™ from Edward Mendell, Co., Inc., N.Y. Such methods are described in U.S. Pat. No. 4,994,276, U.S. Pat. No. 5,128,143 and U.S. Pat. No. 5,135,757, which all describe an excipient system that includes a hydrophilic matrix composed of a heteropolysaccharide and a polysaccharide that can cross link the heteropolysaccharide, and an inert diluent. The specific applicability of these commercially available methods and the formulation of sustained release metoprolol will be discussed in detail below in connection with certain examples of the instant sustained release formulation of sotalol.

In accordance with certain examples, for the preparation of such sustained release sotalol formulations which may be administered to patients on a once-daily basis, or desired longer time interval, certain examples disclosed herein may use the most appropriate methods that have been developed for other compounds (for example, metoprolol) that have been introduced into cardiovascular therapeutics. Having recognized the biochemical similarity of metoprolol and sotalol, and the existence of sustained release formulations of the former, a preferred embodiment of the instant technology may include one or more of the following: a sustained release excipient system comprising the active medicament (e.g., sotalol, or derivatives, analogs, isomers, or the like of sotalol), both hetero- and homo-polysaccharide gums (e.g., xanthan gum and locust bean gum, respectively), a cross-linking agent (e.g., monovalent or multivalent metal cations, in particular calcium sulfate and sodium chloride), and an inert diluent (e.g., lactose, dextrose, sucrose, or mixtures thereof or other pharmaceutically acceptable saccharides). The use of the cross-linking agent with the heteropolysaccharides and homopolysaccharides may result in increased gel-strength and thereby provides a sustained release of sotalol in the environment of use that is suitable for a 24 hour, single dosage, daily administration. However, other preparations and formulations for the sustained release of sotalol over a 24 hour or longer period will be readily selected by the person of ordinary skill in the art, given the benefit of this disclosure.

In accordance with certain examples, and having recognized the biochemical similarity of metoprolol to sotalol, other methods mentioned above for providing sustained release of metoprolol may also be adapted for the formulation of sustained or controlled release oral dosage forms of sotalol. In this regard, the following may also be embodiments of the instant technology: (1) a buoyant controlled release system for sotalol (or an analog, isomer, derivative or the like of sotalol) that includes a pH-dependent polymer that is a salt of alginic acid combined with a pH-independent hydrocolloid gelling agent and binder with a prescribed weight ratio of such salt to such gel all within the range of 0.1:1 to 10:1, for example; (2) a controlled release system for sotalol (or an analog, isomer, derivative or the like of sotalol) that comprises principally a number of beads of sotalol or the like such that a polymer membrane permeable to sotalol or the like coats each of the beads; (3) a "Time Controlled Explosion System" whereby a swelling agent (e.g., a low substituted hydroxypropylcellulose, sodium starch glycolate or carboxymethylcellulose sodium) and a core of the drug sotalol are coated with a water-insoluble coating material (e.g., ethylcellulose); and (4) an oral composition of sotalol or the like that is coated with an anionic polymer soluble at prescribed pH, and a prescribed amount of a water-insoluble polymer from the group of quaternary ammonium substituted acrylic polymers whereby the composition achieves targeted release of the drug in the gastrointestinal tract below the upper part of the small intestine.

In accordance with certain examples, the composition of the present technology may be prepared as pharmaceutically acceptable oral solid dosage forms, such as pills, tablets or capsules. However, as will be explained in more detail below, other sustained release formulations which release sotalol over a time period, preferably of no less than 24 hours, which may be given parenterally, topically, or by way of a body cavity such as the rectum or nose will be readily developed by the person of ordinary skill in the art, given the benefit of this disclosure.

In accordance with certain examples, the present technology is also related to a method of treatment comprising orally (or otherwise) administering the sustained release sotalol to patients, thereby providing therapeutically effective blood levels of medicament for preferably at least about 24 hours. Such methods of treatment, involving once-daily dosage of a sustained release compositions of sotalol, may have a major therapeutic utility in the 24-hour and continuous control of signs and symptoms of a number of cardiovascular disorders. Such methods of treatment would have particular utility in numerous therapeutic settings (as well as others which may be determined by someone skilled in the art, given the benefit of this disclosure) including, but not limited to:

i) Acute control and prevention of the recurrences of life-threatening disorders of rhythm such as ventricular tachycardia and ventricular fibrillation occurring in patients with coronary artery disease;

ii) Prevention of defibrillator shocks in patients with implantable devices for the prevention of sudden death (15, 16),
iii) Termination and prevention of recurrences of atrial fibrillation and flutter in patients with ischemic heart disease as well as heart disease of any etiology;
iv) Prevention of the occurrences of atrial fibrillation by prophylactic administration of sustained release sotalol in patients at high risk undergoing elective cardiac surgery of any etiology;
v) Symptomatic control of angina pectoris in patients still experiencing chest pain after cardiac surgery, after myocardial infarction, or patients with coronary artery disease not amenable to treatment by surgery or angioplasty;
vi) Control of systemic systolic and diastolic high blood pressure for continuous reduction over 24-hours with single dose of the formulation;
vii) Adjunctive therapy for the control of heart rate and atrial fibrillation in the initial acute stages of hyperthyroidism;
viii) Control of atrial fibrillation, myocardial ischemia in the setting of ischemic heart disease, and hypertension simultaneously occurring (as it happens in many elderly patients);
ix) Control of fetal tachycardias through sustained release formulations of sotalol that are suitable for delivery by direct fetal therapy involving intramuscular or intraperitoneal injections; and
x) Other uses of sotalol that have therapeutic activity for any purpose.

In accordance with certain examples, sotalol hydrochloride (4'-(2-isopropylaminoethyl-1-hydroxy)methanesulphonanilide hydrochloride, MW [free base]=308.8 [272.4] g/mol) is a nonselective adrenoceptor-blocking agent at all doses, and at increasing higher doses it produces lengthening of cardiac repolarization in the atrial as well as in ventricular tissues. The drug is a 1:1 racemic mixture of D- and L-sotalol. The beta-blocking activity resides in the L-isomer. The drug is devoid of intrinsic sympathomimetic actions and known to have no effects on blocking sodium-channel activity in heart muscle. Sotalol is absorbed 100% after oral ingestion, there being no first-pass hepatic metabolism and metabolic destruction is negligible. Sotalol is excreted almost completely by the kidneys; renal impairment increases elimination half-life. The mean elimination half-life is about 12 hours; hence, it is typically administered twice daily in equally divided doses. These properties of the drug have been recognized for the currently known formulation of sotalol, and the provision for safety in this regard is the recommendation that patients with a creatinine clearance<60 mL/minute are best excluded from sotalol treatment. After the administration of a dose of current formulation of sotalol, the peak plasma concentration is 2-3 hours. At higher doses of the drug, especially during chronic administration of the short-acting formulation, high peak levels of the drug may lead to proarrhythmic reactions in a small proportion of patients. In contrast, this is less likely in the case of sustained and controlled release formulation of the drug since following ingestion, the peaks and troughs of plasma levels are unlikely to occur, thereby ensuring a greater measure of safety as well as potentially increased efficacy in the treatment of arrhythmias such as atrial fibrillation and flutter, and ventricular tachycardia and fibrillation.

In accordance with certain examples, sotalol hydrochloride reduces the oxygen demand of the heart at rest as well as during activity by slowing heart rate and reducing cardiac contractility and blood pressure, effects which are responsible for its ability to reduce myocardial ischemia and alleviate angina. Another distinct action of the drug slows the conduction down the atrio-ventricular node which will lead to the slowing of the ventricular response in atrial fibrillation and atrial flutter, an effect that is utilized in providing relief from shortness of breath, palpitations, and dizziness, all of which are due to fast heart rates. The prolonging effect of the drug on cardiac repolarization in combination with the drug's anti-adrenergic action is responsible for the beneficial effects on cardiac arrhythmias (17).

In accordance with certain examples, sotalol (also known as Sotacor™, Betapace®, Berlex Pharmaceuticals) is commercially available in the United States as the salt, sotalol hydrochloride. It is normally available as tablets of 80 mg, 120 mg, and 160 mg, with recommended dispensing of each tablet strength twice a day, such that the single daily initiating dose of a sustained release composition described herein could be, for example, 160 mg, intermediate dose 240 mg, and highest dose, 360 mg. In the examples described herein, consideration has been given as to the choice of the method that will be used in the development of sustained-release sotalol to increase the time course of drug action preferably to 24 hours or longer. In this regard, the methods that have been used in the case of metoprolol, a beta-adrenergic drug that has similar structural features, are of particular interest. Both drugs are freely soluble in water, have similar free base MW (metoprolol 267.4; sotalol 272.4), have significantly similar molecular structure, and both drugs are almost completely absorbed, although metoprolol is metabolized with somewhat variable bioavailability. Metoprolol's plasma half-life is in the range of 2.5-9.5 hours and it has been the active medicament of a number of sustained release methods and formulations.

In certain examples, it is specifically contemplated that, by utilization of the methods and formulations articulated in the 24 Hour Release Metoprolol Patent, and recognizing the significant biochemical similarity of sotalol and metoprolol, a sustained release formulation of the three common dosage forms of sotalol may be achieved by utilizing the same or highly similar formulations and methods of formulation known or proposed for metoprolol. In a preferred embodiment, a therapeutically effective amount of sotalol is the active medicament (ranging from a low dose of 160 mg, an intermediate dose of 240 mg, to a high dose of 360 mg, for example, as described above) in a sustained release excipient system is provided.

In accordance with certain examples, one or more gums may also be present in the compositions disclosed herein. In certain examples, the composition may include one or more of a hetero- or homo-polysaccharide gum (e.g., xanthan gum and locust bean gum, respectively), a cross-linking agent (e.g., monovalent or multivalent metal cations, in particular calcium sulfate and sodium chloride), and an inert diluent (e.g., lactose, dextrose, sucrose, or mixtures thereof or other pharmaceutically acceptable saccharides) such that the use of the cross-linking agent with one or more of the heteropolysaccharides and homopolysaccharides results in increased gel-strength and thereby provides a sustained release of sotalol in the environment of use that is suitable for a 24 hour, single dosage, daily administration. For the purpose of this disclosure, the methods and formulations of the 24 Hour Release Metoprolol Patent and any patents in its legal family are incorporated by reference, including all embodiments, preferred or otherwise, articulated therein, that may be applicable to sotalol for the reasons stated above. Specifically, as with metoprolol, the heteropolysaccharide for the purpose of this disclosure would be a water-soluble polysaccharide containing two or more kinds of sugar units, having a branched or helical configuration, and having both significant water-wicking and thickening properties. A preferred polysaccharide for use in the compositions disclosed herein, as is used for the sustained release formulation of metoprolol, is xanthan gum or its derivatives. As with metoprolol, the homopolysaccharide used should preferably be capable of cross-linking with the heteropolysaccharide. In this regard, so called galactomannan gums, comprised solely of mannose and galactose, may be utilized, in particular those which have higher proportions of unsubstituted mannose regions. Locust bean gum is a preferred homopolysaccharide. Moreover, the combination of xanthan gum and locust bean gum is a preferred heteropolysaccharide and homopolysaccharide combination. Because of the similarity of metoprolol and sotalol, the controlled release properties of the sustained release sotalol formulation involving cross-linked gums may be optimal when the ratio of heteropolysaccharide to homopolysaccharide (i.e., galactomannan gums) is from 3:1 to about 1:3, with the same preferred ratio at about 1:1. Nonetheless, as with the sustained release metoprolol formulation, a sustained release excipient may comprise from approximately 1% to approximately 99% by weight heteropolysaccharide gum and from approximately 99% to approximately 1% by weight homopolysaccharide gum. The person of ordinary skill in the art, given the benefit of this disclosure, will be able to select suitable gums, and suitable amounts of the gums, for use in the compositions disclosed herein. As with the metoprolol formulations involving cross-linked gums, the self-buffering properties of xanthan gum and other components of the formulation may allow them to be pH-independent as they move through the gastrointestinal tract and may be substantially impervious to sotalol's solubility.

In accordance with certain examples, a cross-linking agent may also be present in the compositions disclosed herein. As with the metoprolol formulations involving cross-linked gums, certain preferred cationic cross-linking agents may be, for example, calcium sulfate and sodium chloride. Similarly, and for the same reasons, the cross-linking agent may be incorporated relative to the sustained release excipient of the present compositions in an amount of about 1% to 20% by weight of the sustained release excipient. Similarly, the cross-linking agent may be included in an amount approximately 1% to 20% by weight of the final composition. A preferred embodiment, as with metoprolol formulations, will include a cross linking agent that comprises about 10% by weight of the sustained release excipient. Additional cross-linking agents will be readily selected by the person of ordinary skill in the art, given the benefit of this disclosure.

In accordance with certain examples, a diluent may also be present in the compositions disclosed herein. As with the metoprolol formulations involving cross-linked gums, an inert pharmaceutical diluent such as, for example, lactose, dextrose, sucrose or mixtures thereof may be used. Moreover, it is conceivable that a hydrophobic material may be added to the sustained release excipient in such a manner so as to retard hydration of the gums but not disrupt the hydrophilic matrix formed by the gums when they are in the gastrointestinal tract or other environmental fluid. Suitable diluents for a particular sustained release sotalol composition will be readily selected by the person of ordinary skill in the art, given the benefit of this disclosure.

In accordance with certain examples and referring to tablet production for the oral solid dosage form of sotalol derived from a method analogous to the methods described in the 24 Hour Metoprolol Patent, sustained release excipients described above can be combined with sotalol and lubricants and then directly compressed, or may be processed into tablets by conventional wet granulation. More specifically, utilizing the wet granulation methods such as those outlined in the 24 Hour Metoprolol Patent, the prescribed amounts of the heteropolysaccharide gum, the homopolysaccharide gum, the cationic cross linking agent, and the inert diluent may be combined and then subjected to a moistening agent such as water (or alcohol, or the like). The resulting moistened mass may then be dried and milled to the desired particle size using conventional drying and milling methods employed by one skilled in the pharmaceutical arts. It should be noted that wet granulation is a preferred method of preparation for the excipient, noting however that any agglomeration technique may be used to produce a pharmaceutically acceptable excipient. The resulting sustained release excipient may then be combined with sotalol either by way of a V-blender, by wet granulation or by other suitable methods that will be selected by the person of ordinary skill in the art, given the benefit of this disclosure. Before compression into solid dosage form, a pharmaceutically acceptable lubricant may be added; for example, magnesium stearate may be added in an amount of approximately 0.5% to approximately 3% by weight of the solid dosage form. The commercial lubricant Pruv®, produced by Edward Mendell Co., Inc. (Cedar Rapids, Iowa), may be one preferred lubricant as it is with regards to the preparation of solid dosage sustained release metoprolol. Additional lubricants for use in the compositions disclosed herein will be readily selected by the person of ordinary skill in the art, given the benefit of this disclosure.

In accordance with certain examples, hydrophobic materials may be included in the compositions disclosed herein to slow hydration. For example, hydrophobic materials may slow hydration without disruption of the hydrophilic matrix formed by the gums. The hydrophobic material may be, for example, ethylcellulose or any pharmaceutically acceptable hydrophobic materials known to those skilled in the art. Such hydrophobic material may be included in the sustained release excipient of the present compositions in an amount from about 1% to about 20% by weight (more preferably from about 3% to about 12%) and most preferably from about 5% to about 10% by weight of the final product.

In accordance with certain examples, a complete mixture of sustained release sotalol formulation resulting from the methods outlined above (and explained in detail in the 24 Hour Metoprolol Patent), provided that it is enough to make a batch of tablets, may then be processed into tablets using conventional tablet machinery at normal compression pressure. As with metoprolol, however, care should be taken to ensure that it is not over-compressed to such an extent that proper hydration does not occur in the presence of gastrointestinal fluid or the environmental fluid. Because the molecular weight and structural similarities of sotalol and metoprolol, the expected tablet weights may range, for example, from about 300 mg to 950 mg, and the relative weights of drug to tablet may fall within the range specified in the examples outlined in the 24 Hour Metoprolol Patent. For instance, in the examples contained in the 24 Hour Metoprolol Patent, three tablets, each containing 100 mg of metoprolol, were combined with various amounts of the gum in drug:gum ratios of 1:1.77, 1:2.57, and 1:3. In all cases, 24 hour sustained release was achieved in dissolution tests conducted in an automated USP dissolution apparatus. In all cases, as the amount of gum in the formulation was increased, the metoprolol release rate decreased, though all achieved release over a 24 hour period. Indeed, subsequent tests showed that increasing the amount of gum even more relative to the drug resulted in even more prolonged release beyond 24 hours. Similarly, removal of the hydrophobic material (ethylcellulose) from the excipient mixture also resulted in even more prolonged release beyond 24 hours. And finally, tablet size did not appear to affect the release rates.

In accordance with certain examples, recognizing the biochemical similarity of metoprolol and sotalol, and given that it is recognized that sotalol will not interact substantially differently with the excipients, the ratios and methods outlined above and in more detail in the 24 Hour Metoprolol Patent may be suitably adapted for formulation and production of a sustained release (preferably 24 hours or longer) compositions of sotalol. Also, additional and/or alternative methods for preparing the compositions disclosed herein may be found, for example, in U.S. Pat. No. 5,169,638, U.S. Pat. No. 4,792,452, U.S. Pat. No. 4,957,745, U.S. Pat. No. 4,871,549, and U.S. Pat. No. 5,081,154, the entire disclosure of each of which is hereby incorporated herein by reference for all purposes. For example, a buoyant controlled release pharmaceutical powder formulation of sotalol may be produced utilizing the methods articulated in U.S. Pat. No. 5,169,638 (also articulated in related form in U.S. Pat. No. 4,792,452.), particularly in view of the similarities between sotalol and metoprolol and particularly in view of the fact that such powder formulation was particularly adapted for controlled release powder-filled capsules containing metoprolol in its tartrate form. We expect that the amount of sotalol present in the compositions disclosed herein would be 75% by weight, and preferentially up to about 60% by weight. Suitable amounts of sotalol to provide effective amounts in the sustained release compositions disclosed herein, will be readily selected by the person of ordinary skill in the art, given the benefit of this disclosure.

In accordance with certain examples, the composition may also include other components, such as, for example, a water-soluble salt of polyuronic acid (e.g., forms high in guluronic acid as sourced from *Laminaria digitata*, forms high in manuronic acid as derived from *Ascophyllum nodosum*, and other sources) and a pH-independent hydrocolloid gelling agent (such as hydroxypropylmethylcellulose, hydroxypropylcellulose, or methylcellulose). The compositions disclosed herein, free of calcium ions and carbon dioxide producing material(s), may float in gastric juices, and thus prolong the release of the active powder ingredients. The amount of salt of the polyuronic acid will depend on the amount of drug present, with illustrative amounts of polyuronic acid being present in an amount ranging from about 15% to 45% by weight composition, more particularly from about 20% to 40% by weight of the composition. An alginic acid salt is preferred (e.g., potassium alginate, ammonium alginate, and preferably sodium alginate). The hydrocolloid gelling agent may be included in an amount up to 35% by weight of the formulation, and the polyuronic acid salt to hydrocolloid gelling agent weight ratio may be from about 0.1:1 to about 10:1, and more particularly from about 0.4:1 to about 8:1. It should also be noted that the hydrocolloid gel, which may be desirable to include in certain compositions, may be used to provide a viscosity of 50 to 100,000 cPs in a 2% aqueous solution at 20 degrees C. and may have a molecular weight ranging from 80,000 to 300,000.

In accordance with certain examples, the compositions disclosed herein may be prepared in a controlled release preparation involving a number of beads having a soluble component comprising at least about 95% weight/weight of a salt of sotalol and a sotalol permeable polymeric membrane coating enveloping each of the beads. The coating may be ethylcellulose or a mixture of ethylcellulose and hydroxypropylmethylcellulose. In some examples, the coating may be present in amounts such that the sotalol is released through the coating over a period of at least 15 hours virtually independent of pH (in the interval pH 1-8). This method is described in detail with regards to metoprolol in U.S. Pat. No. 4,957,745. Recognizing the biochemical similarities of metoprolol and sotalol, the formulation delineated for metoprolol may be used to easily determine the formulation of a long acting sustained release formulation of sotalol. To achieve such a formulation, sotalol beads may be formed using the following method as adapted from U.S. Pat. No. 4,957,745: in a fluidized bed granulator, sotalol hydrochloride may be sprayed onto the cores of silicon dioxide from a solution of ethanol 95%. The beads or granules which are formed may be covered with the polymeric layer containing ethyl cellulose, hydroxypropylmethyl cellulose and acetyltributylcitrate by applying (through spraying or similar methods) a solution of such substances in methylene chloride and isopropylic alcohol. The coated beads may then be filled or packed into hard gelatin capsules. Variations on the method to achieve a desired configuration, outlined in U.S. Pat. No. 4,957,745 with regards to metoprolol, may employ addition of other additives as well as magnesium-stearate (0.1%), and coating of the tablets in a coating pan.

In accordance with certain examples, another method which may be adapted to preparation of sustained release sotalol compositions is the "Time Controlled Explosion System", outlined in U.S. Pat. No. 4,871,549, whereby a swelling agent (e.g., low substituted hydroxypropylcellulose, sodium starch glycolate or carboxymethylcellulose sodium) and a core of the drug sotalol may be coated with a water-insoluble coating material (e.g. ethylcellulose). The ratio of the drug and the swelling agent in the beads or granules will be readily selected by the person of ordinary skill in the art, given the benefit of this disclosure. Where the desired form is tablet, such oral dosage form may be prepared according to conventional procedure by compressing the mixture of sotalol, swelling agent, diluents and lubricants (e.g., magnesium stearate, etc.). The ratio of the drug and the swelling agent in the tablet may vary depending on the drug and other additives used, and may be determined by one skilled in the art of pharmaceutical preparation using the methods outlined above and in more detail in U.S. Pat. No. 4,871,549. The sustained release pattern for a particular preparation of sotalol may be determined by one skilled in the art of pharmaceutical preparation by adjusting the amount of water-insoluble coating material used and/or by utilizing a method of mixed "lag time" systems in a particular preparation as explained in detail in U.S. Pat. No. 4,871,549.

In accordance with certain examples, another method which may be used to produce a sustained release formulation of sotalol may be adapted from the method outlined in U.S. Pat. No. 5,081,154, where an oral composition of metoprolol succinate is coated with a layer comprising about 10% to about 85% by weight of an anionic polymer soluble at a pH above 5.5, and 15 to 90% by weight of a water-insoluble polymer from the group of quaternary ammonium substituted acrylic polymers. The composition may achieve targeted release of the drug in the gastrointestinal tract below the upper part of the small intestine. Recognizing the biochemical similarity of sotalol and metoprolol, a sustained release formulation may be achieved by applying a similar anionic polymer coating. As proposed with metoprolol succinate, a split dose unit of sotalol may achieve prolonged steady blood plasma levels by administering such a dose with some of the therapeutically active medicament particles having the coating and some of the therapeutically active medicament particles not having the coating. The person of ordinary skill in the art, given the benefit of this disclosure will be able to design suitable spit dose compositions including sotalol.

In accordance with certain examples, other methods and formulations, using other excipient systems, carriers, and/or additives, which achieve the sustained release properties described herein and/or which enable the treatment regimen(s) described herein, will be determined by one skilled and knowledgeable in the art, given the benefit of this disclosure, and are within the scope of the present technology. In particular, there are multiple embodiments, configurations and examples of the instant technology which may include the elements of a sustained release excipient system (e.g., the formulations and methods described in the 24 Hour Release Metoprolol Patent), the therapeutically-active medicament (sotalol hydrochloride, or its derivative, analog, isomer or the like), and certain other elements desirable to provide a sustained release composition. In many cases, the once-a-day or sustained release dosage of sotalol described herein may be pharmaceutically acceptable compositions which comprise a therapeutically-effective amount of sotalol formulated together with one or more pharmaceutically acceptable carriers, additives, and/or diluents, which may be in addition to the pharmaceutically acceptable excipient system used in the sustained release compositions. Such other carriers, additives and/or diluents may be for other purposes such as minimization of side effects, sweetening or taste modification, etc., or may enhance the sustained release formulation in some manner. The pharmaceutical compositions disclosed herein may be specially formulated for administration in solid or is liquid form through various delivery routes, including but not limited to those used, modified, and/or adapted for the following: (1) oral administration, including but not limited to drenches (aqueous or non-aqueous solutions or suspensions), tablets, boluses, powders, granules, pastes for application to the tongue; (2) topical application, including but not limited to a cream, ointment or spray applied to the skin; (3) intravaginally or intrarectally, including but not limited to a suppository, pessary, cream or foam; (4) nasally; or other suitable administration methods that will be readily selected by the person of ordinary skill in the art, given the benefit of this disclosure.

In accordance with certain examples, the compositions disclosed herein may be suitable for oral, nasal, topical (including buccal and sublingual), rectal, vaginal and/or parenteral administration. The formulations may be presented in convenient unit dosage form and may be prepared by any suitable methods known to one skilled in the art of pharmacy. The therapeutically-active quantity of medicament (e.g. sotalol hydrochloride) which can be combined with a carrier material or sustained release excipient system to produce a single dosage form will vary depending upon the host being treated, the particular mode of administration, and other circumstances surrounding the objectives and subject of the treatment. The amount of medicament which can be combined with a carrier material or sustained release excipient system to produce a single dosage form will generally be that amount of the composition which produces a therapeutic effect. As with certain preferred exemplary embodiments described above (i.e. the sustained release excipient system described in the 24 Hour Release Metoprolol Patent as applied to sotalol), the amount of active medicament (e.g. sotalol) and the amount of excipient material, as well as the proportion of one excipient relative to another (e.g. the amount of heteropolysaccharide gum relative to the amount of homopolysaccharide gum relative to the amount of cross linking agent and inert diluent) may be determined by a host of factors, including the desired sustained release, required dosage levels, minimization of side effects, etc.

In accordance with certain examples, sustained release compositions adapted and suitable for oral administration may be in multiple forms including, but not limited to: (1) capsules, cachets, pills, tablets, lozenges (using a flavored basis), powders, granules, (2) a solution or a suspension in an aqueous or non-aqueous liquid, (3) an oil-in-water or water-in-oil liquid emulsion, (4) an elixir or syrup, (5) pastilles and/or as mouth washes and the like. The compositions disclosed herein may also be administered as a bolus, electuary or paste. In certain examples, in solid dosage forms suitable for oral administration (capsules, tablets, pills, dragees, powders, granules and the like), it is possible that the sustained release formulation of sotalol may be mixed with one or more pharmaceutically-acceptable additional ingredients including but not limited to: (1) fillers or extenders, (2) binders, (3) humectants, (4) disintegrating agents; (5) solution retarding agents, (6) absorption accelerators, (7) wetting agents, (8) absorbents, (9) lubricants, and (10) coloring agents. In the case of capsules, tablets and pills, the pharmaceutical compositions may also comprise buffering agents, though it should be noted that certain excipient systems, such as the one proposed by the 24 Hour Release Metoprolol Patent, may exhibit self-buffering and thus may be a pH-independent formulation. Solid compositions, similar in nature, may also be employed as fillers in soft and hard-filled gelatin capsules using excipients that may include, but are not limited, to lactose or milk sugars, high molecular weight polyethylene glycols, and other similar materials.

In accordance with certain examples, a tablet may be made by compression or molding, optionally with one or more accessory ingredients, and by other methods which will be selected by one skilled in the art, given the benefit of this disclosure. Compressed tablets may be prepared using a variety of agents, including but not limited to a binder, a lubricant, an inert diluent, a preservative, a disintegrant, a surface-active agent or a dispersing agent. Molded tablets may be made in a variety of ways known to one skilled in the art, including but not limited to methods that utilize a suitable machine to mold a mixture of the powdered composition moistened with an inert liquid diluent. The suitability of the method for tablet production may depend, for example, on the principal ingredients for the sustained release formulation In accordance with certain examples, the tablets, and other solid dosage forms of the pharmaceutical compositions disclosed herein, such as dragees, capsules, pills and granules, may optionally be scored or prepared with coatings and shells, including but not limited to enteric coatings and other such layering, coverings and coatings well known in the pharmaceutical-formulating art. They may also be formulated so as to provide additional features of controlled release, beyond the sustained release property that is a principal characteristic of the compositions disclosed herein. For example, a composition may be designed such that it releases the active ingredient(s) (e.g., sotalol) only, or preferentially, in a certain portion or portions of the gastrointestinal tract. Variations in the compositions disclosed herein will be readily selected by the person of ordinary skill in the art, given the benefit of this disclosure.

In accordance with certain examples, liquid dosage forms for oral administration of the compositions disclosed herein include, but are not limited to, pharmaceutically acceptable emulsions, microemulsions, solutions, suspensions, syrups, elixirs and the like. The liquid dosage forms may contain inert diluents commonly used in the art, including, but not limited to, water or other solvents, solubilizing agents and emulsifiers, and mixtures thereof.

In accordance with certain examples, oral compositions may also include adjuvants including, but not limited to, wetting agents, emulsifying and suspending agents, sweetening, flavoring, coloring, perfuming and preservative agents. Suspensions, in addition to the active compounds and formulations, may contain suspending agents and the like. Formulations of the pharmaceutical compositions for rectal or vaginal administration may be produced in a number of forms, including but not limited to suppositories, which may be prepared by mixing one or more compositions (e.g., the sustained release formulation including the active medicament sotalol) with one or more suitable pharmaceutically acceptable excipients such as cocoa butter, polyethylene glycol, a suppository wax or a salicylate, and that is/are solid at room temperature, but liquid at body temperature, and thus suitable for storage outside the body and insertion/release/and dispersion in the appropriate body cavity such as the vagina or rectum. Compositions disclosed herein that are suitable for vaginal administration may also include but are not limited to pessaries, tampons, creams, gels, pastes, foams or spray formulations containing such carriers as are known in the art to be appropriate. Dosage forms for the topical or transdermal administration of a compositions disclosed herein may include but are not limited to powders, sprays, ointments, pastes, creams, lotions, gels, solutions, patches and inhalants. The active compounds in the composition may be combined under sterile conditions with a pharmaceutically-acceptable carrier or vehicle, and with any preservatives, buffers, propellants or the likes which may be desired. The ointments, pastes, creams and gels may include, in addition to an active compound, other excipients, which may include but are not limited to: animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound, other excipients which may include but are not limited to lactose, talc, silicic acid, aluminum hydroxide, calcium silicates and polyamide powder, or mixtures thereof. Sprays may also contain propellants, such as chlorofluorohydrocarbons and volatile unsubstituted hydrocarbons, that are standard and customary (as determined by current industry standards) for the production of such materials.

Transdermal patches which deliver the compositions disclosed herein may be produced by dissolving or dispersing the sustained release formulation in the proper medium, which medium would be known by someone skilled in the art of such preparations. Absorption enhancers may also be utilized to maximize and enhance the transdermal delivery of the composition where appropriate. The rate of such transdermal flux can be controlled by a number of ways, including the provision of a rate controlling membrane or dispersion of the sustained release composition in a polymer matrix, gel, or the like.

It should be noted that while unprecedented sustained release formulations of sotalol in oral dosage form have been described herein, injectable solutions and intravenous delivery may also be utilized to effect sustained release sotalol treatment of preferably 24 hours or more. Injectable depot forms of the compositions disclosed herein, which may be rate controlled, may be made by forming microencapsulated matrices of the active medicament in biodegradable polymers or by embedding the active medicament in liposomes or microemulsions that may be safely and effectively used with body tissue. The rate control may depend, at least in part, on the ratio of drug to polymer, and the nature of the particular polymer utilized.

In accordance with certain examples, it is possible that the preparations and formulations disclosed herein may be given through various administration routes including but not limited to oral, topical, and rectal. In all cases, they should be given in forms suitable (from a safety and efficacy standpoint) for each administration route. However, any alternate forms of delivery or administration, including but limited to those outlined above, are feasible. It should also be noted that the various methods, preparations, compositions, and modes of delivery and administration discussed above would be considered and specifically determined by one skilled in the art of pharmaceutical preparations, and the method for using the sustained release formulations (including the preparations, compositions, modes of delivery, administrations, etc.) contemplated in a therapeutic setting will require consideration of the normal range of factors known to one skilled in the medical arts.

In accordance with certain examples, actual dosage levels of sotalol in the pharmaceutical compositions disclosed herein may be adjusted to a level effective to achieve the desired therapeutic response for a particular patient, composition, and mode of administration, without being toxic to the patient. The selected dosage level will depend upon a variety of factors including but not limited to the activity of the particular composition employed, or the ester, salt or amide thereof, the route of administration, the time of administration, the rate of excretion of the particular composition being employed, the duration of the treatment, other drugs, compounds and/or materials used in combination with the particular composition employed, the age, sex, weight, condition, general health and prior medical history of the patient being treated, and like factors well known to one ordinarily skilled in the medical arts. It is contemplated that sustained release sotalol may be administered to humans and other animals for therapy by any suitable route of administration, including but not limited to orally, nasally (e.g., by spray), rectally, intravaginally, intracisternally and topically (e.g., by powders, ointments or drops), buccally and sublingually. Irrespective of the route of administration used, the compositions disclosed herein may be formulated into pharmaceutically-acceptable dosage forms by conventional methods known to those of skill in the art of pharmaceutical preparations.

In accordance with certain examples, a physician or veterinarian having ordinary skill in the art can, using ordinary skill, determine and prescribe an effective amount of the sustained release composition desired. The compositions disclosed herein (i.e., the sustained release formulations) may be formulated for administration in any convenient way for use in human or veterinary medicine, by analogy with other pharmaceuticals.

In accordance with certain examples, it is possible that the molecular structure of sotalol may be altered slightly in the synthesis of the sustained release formulations contemplated by the present disclosure. Such alterations may be desirable to enhance the interaction of the medicament with the other components of the sustained release formulation (e.g., the sustained release excipient system) or for other therapeutic and functional reasons. Such alterations, in addition to the use of sotalol analogs and derivatives as described above, are within the scope of this technology.

In accordance with certain examples, wetting agents, emulsifiers and lubricants, as well as coloring agents, release agents, coating agents, sweetening, flavoring and perfuming agents, preservatives and antioxidants may also be present in the compositions disclosed herein. Additional agents, additives and the like will be readily selected by the person of ordinary skill in the art, given the benefit of this disclosure.

The numbers used in parentheses throughout the disclosure refer to the following citations:

1. Singh B N, Vaughan Williams. The effect of amiodarone, a new anti-anginal drug, cardiac muscle. *Brit J Pharmacol* 1970; 39; 657-667;
2. Singh B N, Vaughan Williams E M. A third class of anti-arrhythmic action. Effects on atrial and ventricular intracellular potentials, and other pharmacological actions on cardiac muscle, of MJ 1999 (sotalol) and AH 3474. *Br J Pharmacol* 1970; 39:675-687;
3. Singh B N: Antiarrhythmic action of dl-sotalol in ventricular and supraventricular arrhythmias. *J Cardiovasc Pharmacol* 2:590, 1992
4. Singh B N: A Symposium: Controlling cardiac arrhythmias with sotalol, a broad-spectrum antiarrhythmic with beta-blocking effects and class III activity. *Am J Cardiol* 65:1A-84A, 1990;
5. Anderson J L: Sotalol in life-threatening ventricular arrhythmias: A unique class III antiarrhythmic. *Amer J Cardiol* 72:1A-80A, 1993;
6. Singh B N. Current antiarrhythmic drugs: An overview of mechanisms of action and clinical utility. *J Cardiovasc Electrophysiol* 1999; 10: 283-301;
7. Singh B N. Sotalol: Current status and expanding indications. *J Cardiovasc Pharmacol Therapeut* 1999; 4 (1): 59-65;
8. The Cardiac Arrhythmia Suppression Trial (CAST) Investigators: Preliminary report: Effect of encainide and flecainide on mortality in a randomized trial of arrhythmia suppression after myocardial infarction. *New Eng J Med* 321:406, 1989;
9. Singh B N: Antiarrhythmic actions of amiodarone: A profile of a paradoxical agent. *Amer J Cardiol* 1996; 78: 41-53;
10. Singh B N (Ed). A Symposium: Approaches to Controlling Cardiac Arrhythmias: Focus on Amiodarone, the last 15 Years. *Am J Cardiol* 1999; 84 (Supp 9A); 1R-174R;
11. Kato R, Yabek L, Ikeda N, Kannan R, Singh B N. Electrophysiologic effects of dextro- and levo-isomers of sotalol in isolated cardiac muscle and their in vivo pharmacokinetics. *J Am Coll Cardiol* 1986; 7:116-126;
12. Antonaccio M J. Gomoll A W Pharmacology, pharmacodynamics and pharmacokinetics of sotalol. *Am J Cardiol* 1990; 65:12A-20A;
13. Nademanee K, Feld G, Hendrickson J A, Singh P N, Singh B N: Electrophysiologic and antiarrhythmic effects of sotalol in patients with life-threatening ventricular tachyarrhythmias. Circulation 1985; 72:555-564;
14. Benditt D G, Williams J H, Jin J et al. for the dl-Sotalol Atrial Fibrillation/Flutter Study Group. Maintenance of sinus rhythm with oral dl-sotalol therapy in patients with symptomatic atrial fibrillation and flutter: A dose-response study. *Am J Cardiol* 1999; 84:270-176;
15. Pacifico A, Hohnloser S, Williams J H et al for the d,l-sotalol implant able cardioverter-defibrillator study group. *N Eng J Med* 1999; 340: 1855-1862;
16. Movsowitz C, Marchlinski F E. Interactions between implantable cardioverter-defibrillators and class III antiarrhythmic drugs. *Am J Cardiol* 82:411, 1998; and
17. Singh B N, Sarna J S M. Mechanisms of action of antiarrhythmic drugs relative to the origin and perpetuation of cardiac arrhythmias. *J Cardiovasc Pharmacol Therapeut* 2001; 6(1):69-87.

Each of the patents and citations listed herein is incorporated herein by reference in its entirety for all purposes. Should the meaning of any term in the patents or citations incorporated by reference conflict with the meaning of any term used in this disclosure, the meaning of the term in this disclosure is intended to be controlling.

When introducing elements of the examples disclosed herein, the articles "a," "an," "the" and "said" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples.

Although certain features, aspects, examples and embodiments have been described above, additions, substitutions, modifications, and alterations of the disclosed illustrative features, aspects, examples and embodiments will be readily recognized by the person of ordinary skill in the art, given the benefit of this disclosure.

What is claimed is:

1. A sustained release composition comprising:
an effective amount of a racemic mixture of D-sotalol and L-sotalol, or
a pharmaceutically acceptable salt thereof; and
a sustained release system, whereby the sustained release system is at least one of a topical, rectal, oral and parenteral system, and is effective to provide sustained release of the racemic mixture of D-sotalol and L-sotalol or the pharmaceutically acceptable salt thereof for at least about 24 hours when exposed to an environmental fluid, and wherein such sustained release composition is for use in the treatment of arrhythmia with reduced beta-blockade and for lengthening cardiac repolarization.

2. The sustained release composition of claim 1, wherein the sustained release system is at least one of a rectal and oral system.

3. The sustained release composition of claim 1, wherein the 24 hours is any other period that is a sustained period relative to conventional drug activity duration and/or half-life of the racemic mixture of D-sotalol and L-sotalol.

4. A sustained release composition comprising: an effective amount of a racemic mixture of D-sotalol and L-sotalol, or a pharmaceutically acceptable salt thereof;
a sustained release excipient system of a heteropolysaccharide gum or a homopolysaccharide gum that is capable of cross-linking;
an inert pharmaceutical diluent; and a pharmaceutically acceptable cationic cross-linking agent capable of cross-linking with the gums and increasing the gel-strength of the gums when exposed to an environmental fluid or environment of use, whereby the sustained release composition is effective to provide sustained release of the racemic mixture of D-sotalol and L-sotalol or the pharmaceutically acceptable salt thereof for at least about 24 hours when exposed to the environmental fluid or the environment of use, and wherein such sustained release composition is for use in the treatment of arrhythmia with reduced beta-blockade and for lengthening cardiac repolarization.

5. The sustained release composition of claim 4, wherein the 24 hours is any other period that is still a sustained period of time relative to conventional drug activity duration and/or half-life of the racemic mixture of D-sotalol and L-sotalol.

6. The sustained release composition of claim 4, wherein the sustained release excipient system is at least one of a topical, rectal, oral and parenteral system.

* * * * *